United States Patent
Caldwell et al.

(10) Patent No.: US 8,062,661 B2
(45) Date of Patent: Nov. 22, 2011

(54) METHODS AND COMPOSITIONS FOR TREATING SKIN WOUNDS

(75) Inventors: Larry J. Caldwell, San Jose, CA (US); Jutaro Shudo, San Jose, CA (US); Andris Adamovics, San Jose, CA (US)

(73) Assignee: Teikoku Pharma USA, Inc., San Jose, CA (US)

( * ) Notice: Subject to any disclaimer, the term of this patent is extended or adjusted under 35 U.S.C. 154(b) by 2092 days.

(21) Appl. No.: 11/002,998

(22) Filed: Dec. 1, 2004

(65) Prior Publication Data

US 2005/0129744 A1    Jun. 16, 2005

Related U.S. Application Data

(60) Provisional application No. 60/529,150, filed on Dec. 11, 2003.

(51) Int. Cl.
  *A61F 13/02* (2006.01)
  *A61L 15/16* (2006.01)
(52) U.S. Cl. ........................................................ 424/448
(58) Field of Classification Search .................... 424/448
  See application file for complete search history.

(56) References Cited

U.S. PATENT DOCUMENTS

| | | |
|---|---|---|
| 4,470,962 A | 9/1984 | Keith et al. |
| 4,769,022 A * | 9/1988 | Chang et al. ............... 604/304 |
| 4,783,257 A | 11/1988 | Morioka et al. |
| 5,175,246 A | 12/1992 | Smith et al. |
| 5,536,502 A | 7/1996 | Mulder |
| 5,645,855 A * | 7/1997 | Lorenz ...................... 424/449 |
| 5,705,485 A | 1/1998 | Cini et al. |
| 6,201,164 B1 | 3/2001 | Wulff et al. |
| 6,342,213 B1 | 1/2002 | Barley et al. |
| 6,548,728 B1 | 4/2003 | Faries, Jr. et al. |
| 2001/0053897 A1 | 12/2001 | Frate et al. |
| 2002/0013300 A1 | 1/2002 | Capelli-Schellpfeffer |
| 2003/0082225 A1 | 5/2003 | Mason |

FOREIGN PATENT DOCUMENTS

| | | |
|---|---|---|
| EP | 0567311 | 10/1993 |
| EP | 0586260 | 3/1994 |
| WO | 199216245 | 10/1992 |
| WO | 2004/071469 A2 | 8/2004 |

OTHER PUBLICATIONS

Bale et al., "A comparison of two amorphous hydrogels in the debridement of pressure sores" Journal of Wound Care, vol. 7, No. 2, pp. 65-68 (1998).
"Clinical result and its effect of hydrogel dressing (IntraSIte Gel) at decubital round", Journal of Japanese Society of Pressure Ulcers, vol. 2, No. 2, p. 179, 39 (2000).

* cited by examiner

*Primary Examiner* — Frederick Krass
*Assistant Examiner* — Benjamin Packard
(74) *Attorney, Agent, or Firm* — Bozicevic, Field & Francis LLP; Bret E. Field; Rudy J. Ng (57) ABSTRACT

Methods of debriding a skin wound are provided. Embodiments of the subject methods include contacting the skin wound with a hydrogel patch debridement composition to debride the wound. Also provided are systems and kits for use in practicing the subject methods.

18 Claims, 2 Drawing Sheets

METHODS AND COMPOSITIONS FOR TREATING SKIN WOUNDS

CROSS-REFERENCE TO RELATED APPLICATIONS

Pursuant to 35 U.S.C. §119 (e), this application claims priority to the filing date of the U.S. Provisional Patent Application Ser. No. 60/529,150 filed Dec. 11, 2003, the disclosure of which is herein incorporated by reference.

INTRODUCTION

BACKGROUND OF THE INVENTION

In general, skin wounds, superficial or deep tissue, afflict a great number of people each year. A multitude of different types of skin wounds exist and vary in cause, severity, healing time, location, etc. For example, while certain wounds heal rapidly, i.e., are acute, many have a relatively prolonged healing time, i.e., are chronic and may persist for weeks, months and even years, where in certain instances a wound may persist that never heals. Accordingly, symptoms or manifestations of wounds may vary and may range from, for example mild abrasions to more severe wounds such as open-skin wounds, e.g., open sores, pustules and ulcerations, and the like, which may be debilitating. Wounds may arise from a number of different causes such as falling and scraping of the skin, burns, vascular insufficiency, e.g., caused by age or disease, etc. Regardless of the cause or particular symptoms, skin wounds need to be treated properly in order to promote effective and efficient healing of the wound. An important determinant in whether a wound heals effectively and efficiently is whether the wound has been effectively debrided.

There are a variety of different techniques and products currently in use to debride wounds which may be broadly classified as surgical/sharp, biosurgical, mechanical, chemical, enzymatic and autolytic. For example, some mild abrasions may be irrigated and scrubbed with soap and water in an attempt to remove foreign matter from the wound such as imbedded dirt and the like. However, this procedure is generally painful to the subject and the washing/scrubbing process may in fact damage viable tissue. Other methods include employing disinfectants such as alcohol or iodine-liberating polymers. However, such methods can cause even more tissue damage than soap and water and may also lead to severe scarring.

Accordingly, there continues to be an interest in the development of new methods and compositions for wound care. Of particular interest is the development of such methods and compositions that are able to effectively debride many different types of skin wounds, are effective at removing a variety of different matter from a skin wound, are easy to use, do not cause undue pain to the subject and which are cost effective.

REFERENCES OF INTEREST

References of interest include the following: U.S. Pat. Nos. 4,470,962; 4,783,257; 5,705,485; 6,342,213; 6,548,728; 6,201,164; and 5,705,485.

SUMMARY OF THE INVENTION

Methods of debriding a skin wound are provided. Embodiments of the subject methods include contacting the skin wound with a hydrogel patch debridement composition to debride the wound. Certain embodiments may include applying an effective amount of an active agent to the skin wound to promote wound healing. Also provided are systems and kits for use in practicing the subject methods.

DETAILED DESCRIPTION OF THE INVENTION

Methods of debriding a skin wound are provided. Embodiments of the subject methods include contacting the skin wound with a hydrogel patch debridement composition to debride the wound. Certain embodiments may include applying an effective amount of an active agent to the skin wound to promote wound healing. Also provided are systems and kits for use in practicing the subject methods.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

The figures shown herein are not necessarily drawn to scale, with some components and features being exaggerated for clarity.

As summarized above, the present invention provides methods and compositions for debriding a skin wound. In further describing the subject invention, the methods and compositions are described first in greater detail, followed by a review of representative applications in which the methods and compositions may be employed. Finally, systems and kits for use in practicing the subject methods are described.

Methods and Compositions

As reviewed above, the subject methods include debriding a skin wound by employing a hydrogel patch debridement composition. Hydrogel patch debridement compositions that may be employed in the practice of the subject invention are described in greater detail below. In general, "hydrogels" are broadly defined herein as aqueous compositions capable of maintaining a gel-like state.

In accordance with embodiments of the subject invention, a hydrogel patch debridement composition is contacted with a skin wound in a manner to adhere any unwanted matter present in or about the skin wound to the hydrogel patch debridement composition. The hydrogel patch debridement composition is then removed along with any unwanted matter adhered thereto.

A feature of the subject hydrogel patch debridement compositions employed in the subject methods is that they are effective at debriding a skin wound. More specifically, the subject hydrogel patch debridement compositions are effective at adhering to and thus removing unwanted matter from a skin wound and are removable from the skin wound without undue pain to the subject. That is, the hydrogel patch debridement compositions are sufficiently cohesive so as to be easily removable from the skin surface, yet unwanted matter present in or about a wound effectively adhere or stick to the hydrogel patch debridement compositions. By "unwanted matter" is meant broadly to refer to any matter present in or about a wound that is in need of removal and includes inorganic matter, and living and non-living organic matter. Unwanted matter may be foreign matter such that it is matter not naturally a part of a subject, i.e., may be from the subject's environment such as organic and inorganic matter, e.g., dirt, tar, gravel, grease, oil, maggots, paper, metals such as iron, or may include the removal of matter that is produced from the subject's body such as loose hair and matter produced as a result of wound breakdown, e.g., slough and devitalized, necrotic tissue or fibrin from a wound and the like. In certain embodiments, the hydrogel patches may facilitate removal or absorption of bodily fluids or exudates from skin.

Thus, in practicing embodiments of the subject invention, a hydrogel patch debridement composition is contacted with a skin wound and removed, where upon removal unwanted matter, if present in or about the skin wound, may adhere to the hydrogel patch debridement composition. That is, the hydrogel patch is removed from the skin wound with any unwanted matter adhered thereto.

In accordance with certain embodiments of the subject methods, after removal of the hydrogel patch debridement composition from the skin wound, at least a second hydrogel patch is contacted with the skin wound. In such embodiments, the wound is sequentially contacted with at least a first and a second hydrogel composition. In these particular embodiments of the invention, the second hydrogel patch may be the same as the first hydrogel patch debridement composition (i.e., identical) or may be different from the first hydrogel patch debridement composition, but in any event is capable of adhering and removing additional and/or newly formed unwanted matter from the skin wound.

Accordingly, to debride a skin wound in accordance with certain embodiments of the subject invention, a first hydrogel patch debridement composition is first removed from any packaging that may be present, and then the protective layer, if present, is removed from the patch, thereby exposing the hydrogel patch debridement composition. In certain embodiments, two or more hydrogel patch debridement compositions may be provided as a single, separable unit, e.g., on the same support. In such embodiments, before use of a hydrogel patch debridement composition, it is separated (e.g., by tearing along a perforation, cutting, etc.) from any other hydrogel patch debridement compositions to which it is attached. In any event, once at least a first hydrogel patch is readied for use, i.e., removed from any packaging and/or separated from any other hydrogel patch debridement compositions, the hydrogel patch debridement composition is then contacted with a skin wound by positioning the hydrogel patch debridement composition over the skin wound.

The skin wound treated in accordance with the subject methods may be in any location on a subject's body, such as arms, hands, legs, feet, face, neck, torso, head (including the face, scalp, etc.) etc. The hydrogel patch debridement compositions conform well to body and wound contours and thus may be employed in any area of the body that has a wound.

The amount of surface area contacted with a hydrogel patch debridement composition will vary depending on the dimensions of the skin wound to be debrided, etc., where the surface area contacted with a hydrogel patch debridement composition is sufficient to provide for the desired debridement of the skin wound. The dimensions of a skin wound debrided according to the subject invention will vary, where the subject invention may be employed with skin wounds of varying dimensions and thus the particular size of a skin wound does not limit the applicability of the subject invention. For example, the surface area of a skin wound that may be debrided in accordance with certain embodiments of the subject invention may range from about 0.1 $cm^2$ or less to about 1000 $cm^2$ or more, e.g., may range from about 1 $cm^2$ or less to about 1000 $cm^2$ or more, e.g., from about 10 $cm^2$ to about 300 $cm^2$, e.g., from about 20 $cm^2$ to about 200 $cm^2$, e.g., about 130 $cm^2$ to about 150 $cm^2$, where in certain embodiments the wound may cover a substantial portion of the truck or even the entire truck or even a good portion of, including all of the entire body of a subject. Accordingly, in certain embodiments the surface area of a skin wound may be as great as about 1000 $cm^2$ to about 5000 $cm^2$ or more, where in certain embodiments the surface may range from about 1 m by about 1 m. For example, in certain embodiments, the subject methods may be employed to debride a wound having a size that ranges from about 0.01 cm to about 20 cm. In certain embodiments, the surface area of a skin wound debrided in accordance with the subject invention may range from, or be less than, about 10 cm by about 14 cm. The depths of skin wounds that may be debrided in accordance with the subject invention vary, where the subject invention may be used to debride wounds of various depths. For example, skin wounds may range from superficial wounds having, e.g., depths as little as about 0.005 mm to about 0.01 mm in certain embodiments to wounds of greater depths such as ranging in depth from, e.g., about 2 mm to about 2.35 mm or more in certain embodiments, e.g., from about 0.007 mm to about 2.3 mm in certain embodiments, e.g., from about 0.01 mm to about 2 mm in certain embodiments, e.g., surgical or tract wounds.

Accordingly, the surface area contacted with a hydrogel patch debridement composition may range from about 1 cm$^2$ or less to about 1000 cm$^2$ or more, e.g., from about 10 cm$^2$ to about 300 cm$^2$, e.g., from about 20 cm$^2$ to about 200 cm$^2$, e.g., about 130 cm$^2$ to about 150 cm$^2$. In certain embodiments, the surface area contacted with a hydrogel patch debridement composition may range from about, or be less than about, 10 cm by 14 cm. In certain embodiments a hydrogel patch debridement composition may be contacted with a substantial portion of a subject's body, e.g., may cover from about 0.001% to about 20% of a subject's body, e.g., may cover from about 0.003% to about 15%, e.g., from about 0.004% to about 10%, such that in certain instances a wound may cover a large part, including substantially all, of a subject's body as noted above, e.g., in the case of a burn, and as such a hydrogel patch debridement composition may be contacted with substantially all, including all, of the wound. For example, in certain embodiments, the surface area contacted with a hydrogel patch debridement composition is sufficient to cover a substantial portion or even the entire truck or substantial portion or even the entire body of a subject. Accordingly, the surface area may range from about 1000 cm$^2$ to about 5000 cm$^2$ or more, where in certain embodiments the surface area contacted by a hydrogel patch debridement composition may range from about 1 m by about 1 m in certain embodiments.

As is described in greater detail below, in representative embodiments the hydrogel patch debridement compositions are self-adhesive, i.e., inherently adhesive, and thus may be fixed in a position over the skin wound, i.e., removably bonded to and/or about a given skin wound, without the use of additional adhesives or other means to hold the patch in place over the formulation. For example, the hydrogel composition matrix may itself be adhesive.

In certain other embodiments a subject hydrogel patch debridement composition may be held in a fixed position about a skin wound using a separate adhesive such as an adhesive backing or the like or a combination of inherent adhesiveness and an additional separate adhesion means may be employed.

In practicing the subject methods, the hydrogel patch debridement composition is contacted with the skin wound for a period of time sufficient to adhere at least some, if not all or substantially all, of the unwanted matter, if present, in or about the skin wound to the hydrogel patch debridement composition. The particular period of time during which the hydrogel patch debridement composition is maintained at the application site depends on a variety of factors such as, but not limited to, the type of the skin wound, the dimensions of the skin wound (e.g., depth, etc.), the age of the skin wound, and the like, but in certain embodiments may generally be at least about 10 seconds, and in certain embodiments the period of time may range from about 30 seconds to about 60 minutes, e.g., about 1 minute to about two hours or more in certain embodiments, e.g., about 15 minutes to about 2 hours or more in certain embodiments, e.g., 30 minutes to about 2 hours or more in certain embodiments, e.g., about 1 hour to about 2 hours or more in certain embodiments. In certain embodiments, contact of the hydrogel patch debridement composition with the skin wound may not exceed about 4 to about 5 hours, e.g., may not exceed about 3 to about 4 hours in certain embodiments, e.g., may not exceed about 2 to about 3 hours in certain embodiments, e.g., may not exceed about 1 to about 2 hours in certain embodiments, such that in many embodiments the contact of the first hydrogel patch with the skin wound may be less than about 2 to about 3 hours, e.g., may be less than about 2 hours in certain embodiments.

Once a sufficient amount of time has elapsed, the hydrogel patch debridement composition is removed from the skin wound. As noted above, the nature of the hydrogel compositions employed in the subject methods enables them to be easily and non-traumatically removed from the skin wound by simply peeling the hydrogel patch debridement composition away from the skin wound. Upon removal, the hydrogel patch debridement composition is removed intact, i.e., the hydrogel patch debridement composition does not leave debris at the site. Also upon removal of the hydrogel patch material, any unwanted matter from in or about the skin wound that has adhered to the hydrogel patch debridement composition is removed along with the hydrogel patch debridement composition. In certain embodiments, the subject methods are highly efficient, such as at least about 50% of the initial amount of unwanted subject matter in the wound (w/w) is removed by the subject methods, where in certain embodiments, the observed percentage of removal is at least about 60%, at least about 70%, at least about 80%, at least about 90% or more, such as at least about 95%, at least about 98%, at least about 99% or more.

As noted above, in addition to the debridement abilities of the hydrogel patch debridement compositions, certain embodiments include removing or absorbing bodily fluids or exudates from skin wound. Thus, the hydrogel patch debridement composition may remove or absorb bodily fluids and exudates such as whole blood, serum, and the like from a skin wound. Whether a given hydrogel patch removes or absorbs/adsorbs bodily fluids or exudates from a wound will at least depend on the water content of the particular hydrogel patch employed. For example, in certain embodiments the subject hydrogel patch debridement compositions have a relatively high water content (e.g., relative to a hydrocolloid composition which differ from hydrogel patch debridement compositions), and as such are limited in their ability to absorb fluids, if at all. That is, in certain embodiments a given subject hydrogel patch debridement composition may have a water content that renders the hydrogel patch debridement composition incapable of absorbing fluid, or absorbing a great amount of fluid. However, in those embodiments where a given hydrogel patch debridement composition is capable of absorbing fluid from a skin wound, the amount of bodily fluid or exudates that may be removed or absorbed by the hydrogel patch debridement composition will vary depending on the particulars of the given fluid, the particulars of a given hydrogel patch debridement composition, etc., but may range from about 0.01 cc/cm$^2$ to about 0.15 cc/cm$^2$ in certain embodiments, e.g., from about 0.03 cc/cm$^2$ to about 0.12 cc/cm$^2$ in certain embodiments, e.g., from about 0.05 cc/cm$^2$ to about 0.1 cc/cm$^2$ in certain embodiments. For example, in certain embodiments a hydrogel patch debridement composition having a gel base with a weight of about 1000 grams/m$^2$ and a water content of about 50%, about 1 cc/cm² of bodily fluid or exudate may be absorbed by this hydrogel patch debridement composition.

As described above, in certain representative embodiments, more than one hydrogel patch composition (i.e., at least two hydrogel patch debridement compositions) are sequentially contacted with a skin wound to debride the skin wound. According to such embodiments, once the first hydrogel patch is removed from the skin wound, at least one more hydrogel patch debridement composition is then contacted with the skin wound. A second hydrogel patch debridement composition contacted with the skin wound may be the same type (i.e., identical type) of hydrogel patch debridement composition as the first hydrogel patch debridement composition, or may be a different type such that a second hydrogel patch debridement composition may differ from the first in at least one aspect such as the second hydrogel patch debridement composition may include the addition of one or more components not present in the first hydrogel patch debridement composition, the second hydrogel patch debridement composition may lack one or more components present in the first hydrogel patch debridement composition, the second hydrogel patch debridement composition may include different concentrations of one or more components than that of the first hydrogel patch debridement composition, the second hydrogel patch debridement composition may have different dimensions of the hydrogel patch debridement composition than the first hydrogel patch debridement composition, etc.

Accordingly, a feature of certain representative embodiments of the subject methods is that the subject methods include at least two debridement steps: (1) a first debridement with a first hydrogel patch debridement composition, and (2) at least a second debridement with a second hydrogel patch debridement composition. In this manner, the subject methods may enable more thorough debridement of a wound. For example, in instances where contact with the skin wound with the first hydrogel patch does not result in all unwanted matter removed from the wound and/or in instances where unwanted matter is continuously produced (i.e., matter is deposited in or around the skin wound after the removal of the first hydrogel patch debridement composition), the subject methods provide a thorough and/or continual debridement.

In contacting the skin wound with a second hydrogel patch debridement composition, the second hydrogel patch is first removed from any packaging that may be present and/or separated from any other hydrogel patch compositions if attached thereto, and the protective layer, if present, is removed from the second hydrogel patch debridement composition, thereby exposing the second hydrogel patch debridement composition. The hydrogel patch debridement composition is then contacted with the skin wound by positioning the hydrogel patch debridement composition over the skin wound in a manner analogous to that described above for the first hydrogel patch debridement composition.

The period of time between the removal of the first hydrogel patch debridement composition from the skin wound and the contact of the second hydrogel patch debridement composition to the skin wound may vary, but is usually minimal such that the second hydrogel patch debridement composition is typically contacted with the skin wound within a minimal amount of time following removal of the first hydrogel patch debridement composition. For example, in certain embodiments, the second hydrogel patch debridement composition may be contacted with the skin wound in less than about 10 seconds to about 90 minutes after removal of the first hydrogel patch debridement composition. Embodiments may also include contacting a second hydrogel patch composition with the skin wound in less than about 10 seconds and greater than about 90 minutes after removal of a first hydrogel patch composition.

The second hydrogel patch may be contacted with the same surface area of the wound as the first hydrogel patch or may be contacted with a different surface area, but at least a portion of the skin wound contacted with the first hydrogel patch is contacted with the second hydrogel patch. For example, the first hydrogel patch may be contacted with all of the skin wound and the second hydrogel patch may be contacted with a portion of the skin wound, or vice versa, but in any event there is at least some area of the skin wound that is contacted with at least the first and second hydrogel patch debridement compositions. The amount of time the second hydrogel patch is contacted with the skin wound may be the same amount of time as the first hydrogel patch was contacted with the skin wound, or may be contacted with the skin wound for more or less time than the first hydrogel patch debridement composition. The period of time the second hydrogel patch may be contacted with the skin wound may depend on, e.g., whether further debridement of the wound is necessary. The period of time the second hydrogel patch may be contacted with the skin wound may generally be at least about 10 seconds and in certain embodiments the period of time may range from about 30 seconds to about 60 minutes, e.g., about 1 minute to about two hours or more, e.g., about 15 minutes to about 2 hours or more, e.g., 30 minutes to about 2 hours or more, e.g., about 1 hour to about 2 hours or more. In certain embodiments, contact of the second hydrogel patch debridement composition with the skin wound may not exceed about 4 to about 5 hours, e.g., may not exceed about 3 to about 4 hours, e.g., may not exceed about 2 to about 3 hours, e.g., may not exceed about 1 to about 2 hours, such that in many embodiments the contact of the second hydrogel patch with the skin wound may be less than about 2 to about 3 hours, e.g., may be less than about 2 hours.

Once the second hydrogel patch debridement composition is contacted with the wound for a sufficient amount of time, the second hydrogel patch is removed from the wound. Analogous to that described above for the first hydrogel patch debridement composition, any unwanted matter that has adhered to the second hydrogel patch is this also removed from the wound along with the second hydrogel patch debridement composition.

Following removal of the second hydrogel patch, in certain embodiments, the subject methods may include contacting the skin wound with one or more additional hydrogel patch debridement compositions. The exact number of hydrogel patch debridement compositions employed in the treatment of a particular skin wound may vary depending on the type of wound, the amount of time wound takes to heal, etc. For example, as at least two hydrogel patch debridement compositions are employed, the number of hydrogel patch debridement compositions that may be employed in the debridement of a given skin wound may range from 2 to about 50 or more, e.g., from about 2 to about 20, e.g., from about 2 to about 10. For example, in certain embodiments, the initial stages of healing (e.g., the first 24 hours after a skin wound is provided) may include the use of up to about 50 hydrogel patch compositions, such that hydrogel patches may be continually contacted with the skin wound and removed and replaced with another hydrogel patch debridement composition throughout the course of 24 hours. The amount of time a hydrogel patch debridement composition may be replaced, for example during the course of a day may range from at least two times to up to as much as 48 times in the 24 hour period (e.g., once per 30 minutes), e.g., 24 times in the 24 hour period (e.g., once per hour), e.g., 12 times in the 24 hour period (e.g., once every two hours), etc. Hydrogel patch debridement compositions employed after the removal of the second hydrogel patch debridement compositions may be the same type or a different type of any hydrogel patch debridement compositions contacted with the skin wound previously. For example one or more additional hydrogel patch debridement composition (i.e., a third, fourth, fifth, sixth, seventh, etc. hydrogel patch debridement composition) may differ from one or more previously used hydrogel patch debridement compositions in at least one aspect such as one or more additional hydrogel patch debridement compositions may include the addition of one or more components not present in one or more hydrogel patch debridement composition used previously, one or more additional hydrogel patch debridement compositions may lack one or more components present in or more hydrogel patch debridement compositions used previously, one or more additional hydrogel patch debridement compositions may include different concentrations of one or more components than that of one or more previously used hydrogel patch debridement composition, one or more additional hydrogel patch debridement compositions may have different dimensions of the hydrogel patch debridement composition than one or more previously used hydrogel patch debridement composition, etc.

As noted above, certain representative embodiments include applying an effective amount of a pharmaceutically active agent to the skin wound, where such may be applied before, during or after contacting the skin wound with a hydrogel patch debridement composition. By effective amount is meant a dosage sufficient to provide the desired result. For example, if the active agent is an anesthetic, an effective amount is that which provides the desired anesthetic result. As will be apparent to those of skill in the art, the effective or optimal amount will vary depending on the particular active agent employed, the particular wound being treated, etc. In certain embodiments, multiple applications of an effective amount of one or more active agents may be applied to a given skin wound, where some or all of such applications may include the same or different active agents. Thus, in accordance with the subject invention once an appropriate active agent is selected, an effective or optimal amount of the active agent is applied to or about the skin wound being debrided.

The effective amount of active agent may be a separate component from the hydrogel patch debridement composition or may be integrated into the hydrogel patch debridement composition itself. Accordingly, application of the active agent may be accomplished in any convenient manner and may be dictated at least in part by the form in which the active agent exists, i.e., whether the active agent is present in the hydrogel patch debridement composition itself or as a separate components in the form of a separate granules, aerosol, cream, lotion, ointment, gel, solution, foam, powder, etc. Thus, the pharmacological agent may be incorporated into a variety of formulations for therapeutic administration. More particularly, the agents may be formulated into pharmaceutical compositions by combination with appropriate, pharmaceutically acceptable carriers or diluents, and may be formulated into preparations in solid, semi-solid, liquid or gaseous forms. Accordingly, the mode of administration will be dictated by the form in which the active agent is present. For example, if present as a separate component from the hydrogel patch debridement composition, the active agent may be sprayed onto a skin wound, rolled-onto a skin wound, poured onto a skin wound or the active agent may be applied to a skin wound using a swab, finger, syringe, and the like. Other protocols for applying an active agent to a skin wound are known to those of skill in the art and may be employed in accordance with the subject methods. In those embodiments where the active agent is integral with a given hydrogel patch debridement composition, the active agent is thus applied to the skin wound upon contact of the active agent-containing hydrogel patch debridement composition to the skin wound.

The amount of surface area upon which the active agent is applied may vary depending on the particular skin wound, the particular active agent employed, etc., where the active agent may be applied to all or only part of the skin wound being debrided. In any event, the surface area that is contacted with the active agent is generally sufficient to provide for the desired amount of agent administration, and in many embodiments an active agent is applied to a surface area having dimensions analogous to that described above for dimensions that may be contacted with a hydrogel patch debridement composition.

A variety of different pharmaceutically active agents may be employed, where the particular active agent(s) used will be dictated by the particulars of a given wound, etc. Water soluble and water insolubale active agents may be employed. Active agents of interest include, but are not limited to, anesthetics to relive pain and itching, antiinflammatories, antimicrobials, antibiotics and antiseptics to retard infection, growth factors to promote tissue growth, etc. Accordingly, the particular active agent(s) is selected for use depending on the particular circumstances of the skin wound to be treated. For example, if the wound is a skin ulcer then one or more active agents that promote healing of skin ulcers may be employed (e.g., sodium hyaluronate or the like); if the wound is a burn then one or more active agents that promote healing of burns may be employed (e.g., an antimicrobial such as silver sulphadiazine or a derivative thereof or the like); if the wound may produce a scar then one or more active agents that reduce the incidence or severity of scarring may be employed. For example, in regards to preventing or reducing the severity of scarring, one or more of an nonsteroidal anti-inflammatory agent, antihistamine, interferon, agent that inhibits collagen cross-linking such as putrescine, agent that stimulates proteolytic enzyme synthesis, e.g., by increasing the degradation rate of collagen and matrix proteins such as calmodulin and protein kinase C inhibitors, agent that inhibits the incorporation of protein into extracellular matrix protein such as a calcium channel blocker, and the like, may be employed.

More specifically, suitable active agents which may be used in accordance with the subject invention include, but are not limited to, antimicrobials, including antibacterial agents including aminoglycoside antibiotics, beta-lactam antibiotics, clofazimine, pimaricin, cefoxitin, n-formamidoyl thienomycin and other thienamycin derivatives, amphotericin, choramphenical, tetracyclines, sulfacetamide, mupirocin, chloramphenicol, neomycin, gramicidin, bacitracin, chlorhexidine, nitrofurazone, sulfonamides; gentamycin, kanamycin, amikacin, sisomicin and tobramycin; nalidixic acid and analogs such as norfloxacin, silver sulphadiazine or a dervitive thereof such as cerium nitrate-silver sulphadiazine, silver nitrate, and the antimicrobial combination of fludalanine/pentizidone; nitrofurazones, anti-infectives and antiseptics such as iodine, chloramines, benzalkonium chloride, phenol and the like; antiinflammatories including nonsteroidal antiinflammatory agents (NSAIDs) such as salts and derivatives of ketoprofen, flurbiprofen, felbinac, and diclofenac, cortisone, hydrocortisone, betamethasone, dexamethasone, fluocortolone, prednisolone, triamcinolone, indomethacin, sulindac, its salts and its corresponding sulfide, and the like; anesthetics such as benzocaine, lidocaine, dibucaine, butamben, butanilicaine, ethyl aminobenzoate, fornocaine, hydroxyprocaine, isobutyl p-aminobenzoate, naepaine, octacaine, parethoxycaine, piridocaine, prilocaine, procaine, risocaine, tolycaine, trimecaine, tetracaine, xylocaine, ethylaminobenzoate (benzocaine), and the like; analgesics such as methyl salicylate, menthol, camphor, methyl nicotinate, triethanolamine salicylate, glycol salicylate and salicylamide and the like; antifungal agents such as tolnaftate, undecylenic acid, salicylic acid, zinc undecylenate and thiabendazole and the like; antimycotics; antiparasitic compounds such as ivermectin; and antiviral effective compounds such as idoxuridine, acyclovir and interferon; enzymes and enzyme inhibitors such as plasmin-type enzymes capable of digesting thrombin such as fibrinolysin; growth factors such as polypeptide growth factors including, e.g., epidermal growth factor, acidic fibrogeblast growth factor, basic fibroblast growth factor, platelet dervided growth factor, transforming growth factor-alpha, transforming growth factor-beta, angiogenin, nerve growth factor, insulin-like growth factors (IGF-I, IGF-II) or mixtures thereof; steroids; insulin; aloe vera; herbal extracts such as gotu kola (*Centella asiatica*), and the like; collagen; vitamins; minerals such as zinc and the like; papaya; hyaluronic acid salts and derivatives such as sodium hyaluronate; glucocorticoids; antihistaminics such as doxepin (Prudoxin); antioxidants; calmodulin; protein kinase C; calcium channel blockers; desoxyribonucleosides; and the like, where any of the foregoing may be isolated from natural sources, produced by recombinant technology or chemical synthesis.

As noted above, one or more steroidal agents may be employed. Thus, in accordance with the subject invention, any class of steroid may be employed in accordance with the subject invention. That is, Class I steroids (very potent steroids), Class II steroids (potent steroids), Class III steroids (moderately potent steroids) and Class IV steroids (relatively mild steroids), etc., may be used with the subject invention. A variety of steroids that may be employed in accordance with the subject invention include, but are not limited to: triamcinolone, triamcinolone acetonide, clobetasol, clobetasol propionate, clobetasone butyrate, desonide, alclometasone, flurandrenolide, desoximetasone, betamethasone, loteprednol, fluorometholone, difluprednate, mometasone furoate, diflorasone diacetate, diflucortolone valerate, fluocinonide, amcinonide, halcinonide, fluocinolone acetonide, flumetasone pivalate, corticosteroids such as hydrocortisone, hydroxyltriamcinolone, alpha-methyl dexamethasone, dexamethasonephosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone. A combination or mixture of one or more of the above dermatological agents may be employed.

A combination of any of two or more active agents may be contacted with a given skin wound simultaneously or sequentially. For example a first active agent may be employed before or at the same time as the first debridement with a first hydrogel patch debridement composition and a second active agent may be employed after the first debridement, e.g., before, at the same time or after the second debridement with a second hydrogel patch debridement composition. For example, a local anesthetic may be employed in conjunction with debridement using a first hydrogel patch debridement composition and an antibiotic may be employed in conjunction with debridement using a second hydrogel patch debridement composition. Still further, one or more agents that prevent or reduce the severity of scarring may be employed, for example after removal of the second hydrogel patch debridement composition. For example, an anti-scarring agent may be employed in conjunction with a third, fourth, fifth, sixth, etc., hydrogel patch debridement composition.

Hydrogel Patch Debridement Compositions

In general, a hydrogel patch debridement composition employed in the subject methods includes a gel base or gel matrix, where in representative embodiments the gel base is an adhesive gel base, e.g., such that the gel base is itself adhesive. In representative embodiments, the hydrogel compositions are adhesive, as determined using the Japanese Industrial Standards (JIS) Z-0237 adhesive strength measurement protocol (see e.g., the Experimental Section, below). A given hydrogel composition is considered to be adhesive if it stops at least a No. 3 size ball, such as at least about a No. 4 size ball, including at leasta bout a No. 5 size ball, in this protocol. In certain embodiments, the composition is sufficiently adhesive to stop a No. 6 ball or greater, e.g., No. 7 ball or greater, e.g., No. 8 ball or greater, e.g., No. 9 ball or greater. In certain embodiments, the subject compositions are differentially adhesive, in that they show greater adehesiveness to non-living, as opposed to living matter.

In general, the subject hydrogel patch debridement compositions are made up of a water-soluble high molecular weight substance, e.g., a water-soluble polymer, water and a water retaining agent.

Water-soluble high molecular weight substances of interest include water-soluble polymers, where polymers of interest include, but are not limited to: gelatin, starch, agar, mannan, alginic acid, polyacrylic acid, polyacrylate such as sodium polyacylate, dextrin, methylcellulose, sodium methylcellulose, hydroxypropylcellulose, sodium carboxymethylcellulose, cellulose gum, carboxyvinyl polymer, polyvinyl alcohol, polyvinylpyrrolidone, Arabia gum, acacia, tragacanth gum, karaya gum, and starch acrylate copolymer or other starch sodium acrylate graft copolymers. Metallic salts of these, as well as the products of cross-linking these by means of organic or inorganic cross-linking agents, are also of interest. Specifically, cross-linking agents may be included in the subject hydrogel patch debridement compositions, where exemplary cross linking agents include, but are not limited to: dried aluminum hydroxy gel, dihydroxy aluminum acetate, magnesium aluminometasilicate, aluminum hydroxide, magnesium metasilicate aluminate, synthetic aluminum silicate, calcium hydroxide, aluminum ammonium sulfate, and calcium chloride. These water-soluble polymers may be used to bring out the properties and characteristics of the other starting materials used in the hydrogel patch debridement composition, and in practice can be used alone or in combinations of 2 or more. The amount of water soluble high molecular weight substance(s) present in the adhesive gel base may range from about 0.5% to about 20% (w/w), usually from about 2 to 15% (w/w) and the amount of cross-linking agent cross-linking agent present may range from about 0.001% to about 2% (w/w), e.g., from about 0.003% to about 1.5% (w/w), e.g., from about 0.05% to about 1% (w/w)

While any convenient water may be employed as the water component, of interest are distilled water or ion-exchange water or the like. The amount of water present in the hydrogel patch debridement composition is sufficient to impart the desired physical properties to the hydrogel patch debridement composition. The amount of water will vary depending on the particular high molecular weight substance(s) employed, etc., where typically the amount of water in the hydrogel patch debridement composition is at least about 25% water by weight, and more usually at least about 30% water (w/w). For example, typically the amount of water ranges from about 25% (w/w) to about 90% (w/w), usually from about 20% (w/w) to about 80% (w/w), where in certain embodiments the amount of water ranges from about 30% (w/w) to about 50% (w/w), e.g., from about 30% (w/w) to about 40% (w/w).

The water-retaining agent or water-holding agent of the subject hydrogel patch debridement compositions is any agent that is capable of at least diminishing the volatilization of water contained in the hydrogel patch debridement composition base so that the water content in the hydrogel patch debridement composition base is maintained at least a substantially constant, if not constant, level during storage and use of the hydrogel patch debridement composition. One or more water-retaining agents may be employed in the subject compositions, where the amount of water-retaining agent present in the adhesive gel base generally ranges from about 1 to about 40% by weight, usually from about 3 to about 30% by weight. Examples of suitable water-retaining or water-holding agents include, but are not limited to: one or more types of polyvalent or polyhydric or sugars or alcohols, such as glycerin, sorbitol such as D-sorbitol, propylene glycol, diethylene glycol, 1,3-butylene glycol, and ethylene glycol, and the like.

In addition to the aforementioned ingredients, various additives may also be employed, such as, but not limited to inorganic substances such as kaolin, bentonite, and titanium dioxide; preservatives such as paraben; anionic, cationic, and nonionic surfactants; metallic aluminum crosslinking agents such as aluminum chloride, dried aluminum hydroxide gel, and dihydroxyaluminum aminoacetate; oils such as jojoba oil and castor oil; chelating agents such as EDTA; pH regulators such as malic acid, tartaric acid, and diisopropanolamine; alcohols such as ethanol; moisture retaining agents such as hyaluronic acid, aloe extract, and urea; and other perfumes and coloring agents.

The pH of the hydrogel patch debridement compositions typically is one that lies in a physiologically acceptable range, where the pH typically ranges from about 3.0 to 8.0 and more typically ranges from about 4.0 to 7.0. As noted above, one or more active agents may be includes in the hydrogel patch debridement compositions. A diverse array of active agents or ingredients may be present in the hydrogel patch debridement compositions, as described above. Depending on the nature of the agent, the amount of active agent present in the composition may ranges from about 0.2 to 10%, e.g., from about 0.2 to 5%, e.g., from about 0.5 to 5%.

In certain embodiments, a hydrogel patch debridement composition (i.e., the water-soluble polymer gel, water and water retaining agent) may be present on a support or backing. The support is generally made of a flexible material which is capable of fitting in the movement of the human body and includes, for example, various non-woven fabrics, woven fabrics, spandex, flannel, or a laminate of these materials with polyethylene film, polyethylene glycol terephthalate film, polyvinyl chloride film, ethylene-vinyl acetate copolymer film, polyurethane film, and the like. By "flexible" it is meant that the support may be substantially bent or folded without breaking, tearing, ripping, etc. The support may be porous or non-porous, but is typically non-porous or impermeable to the hydrogel composition, active agent if employed and fluids, e.g., any fluids exuded from the wound site.

The length and width dimensions of the support are typically substantially commensurate, including exactly commensurate, with the length and width dimensions of the hydrogel patch debridement composition with which it is associated. The support layer typically may have a thickness that ranges from about 10 µm to about 1000 µm, but may be less than about 10 µm and/or greater than 1000 µm in certain embodiments.

In addition to the hydrogel patch debridement composition and the optional support layer, the subject patches may also include a release film on the surface of the hydrogel composition layer opposite the backing that provides for protection of the hydrogel composition layer from the environment. The release film may be any convenient material, where representative release films include polyesters, such as PET or PP, and the like.

The hydrogel patch debridement composition may be fabricated using any convenient protocol. One convenient protocol for fabrication of the subject patches includes preparing a hydrogel patch debridement composition paste through the uniform mixing of the aforementioned ingredients and then coating the paste onto the support if employed, followed by cutting of the resultant product to the specified size to obtain the desired hydrogel patch debridement composition. The shape of the patch may vary, where representative shapes include square, rectangle, oval, circle, triangular, etc. The size of the patch may also vary, where in many embodiments the size ranges from about 1 $cm^2$ or less to about 1000 $cm^2$ or more, e.g., in certain embodiments ranges from about 10 to about 300 $cm^2$, e.g., from about 20 to about 200 $cm^2$, e.g., about 130 $cm^2$ to about 150 $cm^2$. As noted above, in certain embodiments, the surface area is sufficient to cover a substantial portion or even the entire truck or even a substantial portion of the entire body or even the entire body of a subject. Accordingly, the surface area may range from about 1000 $cm^2$ to about 5000 $cm^2$ or more, where in certain embodiments the dimensions of a subject hydrogel patch may be about 1 m by about 1 m. For example, in certain embodiments a hydrogel patch debridement composition may be a full body wrap composition. For a more detailed description of an exemplary fabrication protocol, see for example U.S. Pat. No. 5,827,529, the disclosure of which is herein incorporated by reference. It should be noted that the above manufacturing protocol is merely representative. Any convenient protocol that is capable of producing the subject hydrogel patch debridement compositions, as described above, may be employed.

Certain hydrogel patch debridement compositions may be adapted and employed for use with the subject invention. Representative hydrogel patch debridement compositions that may be adapted for use with the subject invention include, but are not limited to those described in PCT International Publication Nos.: WO 02/078757 and WO 02/078756 and U.S. Pat. Nos. 5,120,544; 5,160,328; 5,270,358; 5,423,737; 5,476,443; 5,489,262; 5,501,661; 5,827,529; 6,039,940; 6,096,333; 6,214,374; 6,296,869; 6,348,212; 6,455,065; the disclosures of which are herein incorporated by reference.

Figure 1:
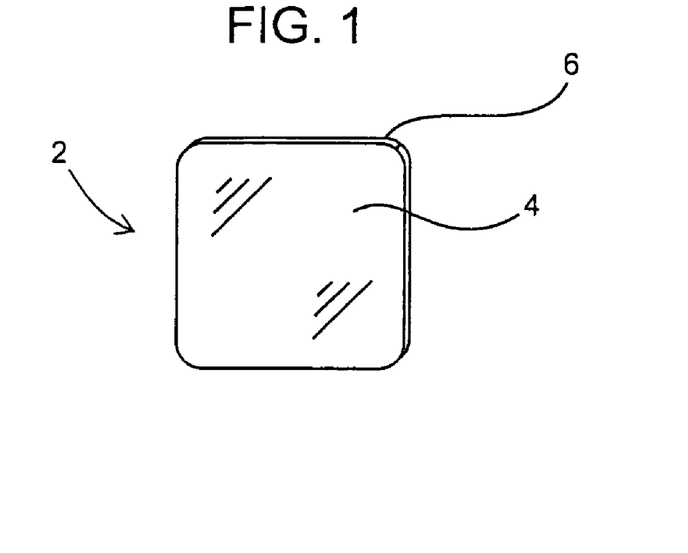
FIG. 1 shows an exemplary embodiment of a subject hydrogel patch debridement composition.

An exemplary embodiment of a subject hydrogel patch debridement composition is shown in FIG. 1 and includes a hydrogel patch debridement composition 4 and an optional support 6 on which the hydrogel patch debridement composition is positioned, collectively referred to in FIG. 1 as element "2". In this particular embodiment, the hydrogel patch debridement composition is rectangular, however this shape is not intended to limit the invention as other shapes are possible as well such as circular, square, triangular, etc., or may be a complex or irregular shape.

Utility

The subject methods find use in any application in which the debridement of a wound of a subject is desired. Generally, such subjects are "mammals" or "mammalian", where these terms are used broadly to describe organisms which are within the class mammalia, including the order carnivore (e.g., dogs and cats), rodentia (e.g., mice, guinea pigs, and rats), and primates (e.g., humans, chimpanzees, and monkeys). In many embodiments, the subject is a human. Accordingly, the subject methods may be used to treat a wide variety of open- and closed-skin wounds such that the subject methods may be used to debride wounds that have resulted from a variety of causes, e.g., as a result of a condition such as a disease state, a physical injury such as a fall, scrape, stab wound, gun shot, surgical wound, infection, etc., wartime injuries such as bombs, bullets, shrapnel. Likewise, the subject methods may treat wounds of various dimensions. For example, the subject methods may be employed to debride both deep tissue wounds and shallow or superficial wounds, where certain wounds may have depths that reach the muscle. Accordingly, wounds that may be debrided in accordance with the subject methods may be confined to the epidermis such that they do not penetrate into the dermal layer, may be as deep as the dermis or deeper, e.g., may penetrate to or through the dermis and even to or through the subcutaneous tissue layer or deeper, e.g., may penetrate through or to the muscle layer or further. For example, the subject methods may be used to debride wounds that having a depth that ranges from about 0.005 mm to about 2.35 mm, e.g., from about 0.007 mm to about 2.3 mm, e.g., from about 0.01 mm to about 2 mm The subject methods may also be employed to debride wounds of various sizes (i.e., various lengths, widths) and shapes. For example, in certain embodiments the subject methods may be employed to debride wounds that may be characterized as relatively small, e.g., with respect to the total surface area of the subject's body. As noted above, in certain embodiments the subject methods may be employed to debride wounds that may be characterized as relatively large, e.g., with respect to the total surface area of the subject's body. For example, in certain embodiments the subject methods may be employed to debride a wound that covers substantially all, including all, of a subject's trunk and even substantially all, including all, of a subject's entire body. For example, in certain embodiments, the subject methods may be employed to debride a wound having a size that ranges from about 0.01 cm to about 20 cm. In certain embodiments the subject methods may be employed to debride a wound having a size that ranges from about, or is less than about, 10 cm by about 14 cm. Types of wounds that may be treated with the subject invention include, but are not limited to, ulcers, including pressure ulcers, diabetic ulcers (e.g., diabetic foot ulcers), venous ulcers, lower leg ulcer, etc.; burns (first, second and third degree burns) including scalds, chemical burns, thermal burns such as flame burns and flash burns, ultraviolet burns, contact burns, radiation burns, electrical burns, etc.; bone infections (osteomyelitis); gangrene; skin tears or lacerations, such as made by knives, etc.; abrasions; punctures such as made by nails, needles, wire, and bullets, etc.; incisions such as made by knives, nails, sharp glass, razors, etc.; avuls; amputations; post-operative infections; surgical wounds; brown recluse spider wounds; failing or compromised skin/muscle grafts or flaps; bites; slash wounds, i.e., a wound where the length is greater than the depth; bruises; and the like, or a combination of one or more of the above.

Systems

The subject invention also includes systems for use in practicing the subject methods. The subject systems include one or more, e.g., at least two, hydrogel patch debridement compositions, where any two or more hydrogel patch debridement compositions of a system may be the same or may be different, e.g., differ in at least one aspect. One or more of the hydrogel patch debridement compositions may be present on a support or backing, e.g., a non-porous support, as described above.

The subject systems may also include one or more active agents, which may be integrated with one or more hydrogel patch debridement compositions or may be separate components from one or more hydrogel patch debridement composition. In certain embodiments, one or more hydrogel patch debridement compositions may have an active agent integrated therewith and one or more hydrogel patch debridement composition may lack an integrated active agent, e.g., an active agent may be a separate component. In those embodiments that include one or more separate active agents, an active agent delivery component may be included, e.g., a syringe, swab, etc.

Kits

Also provided are kits, where the subject kits at least include at least one hydrogel patch debridement composition. In certain embodiments, the kits may include two or more hydrogel patch compositions, which may be the same or may be different, e.g., differ in at least one aspect. One or more of the hydrogel patch debridement compositions present in the subject kits may be present on a support or backing, e.g., a non-porous support, as described above. In certain embodiments, more than one hydrogel patch debridement composition may be sealed together within a single packaging. However, typically each hydrogel patch debridement composition present in the kit is sealed in an individual package so that one hydrogel patch debridement composition may be removed from its packaging and used while the packaging of any other hydrogel patch debridement compositions of the kit remains intact or un-breached. In certain embodiments, two or more hydrogel patch debridement compositions may be present on a single support.

The subject kits also include instructions for how to use the hydrogel patch debridement compositions to debride a skin wound according to the subject invention. The instructions are generally recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The subject kits may also include one or more active agents, which may be integrated with the patch compositions or may be separate components of the kit.

In certain embodiments, one or more hydrogel patch debridement compositions of a given kit may have an active agent integrated therewith and one or more hydrogel patch debridement composition may lack an integrated active agent, e.g., an active agent may be a separate component. In those embodiments that include one or more separate active agents, an active agent delivery component may be included, e.g., a syringe, swab, etc.

Figure 2:
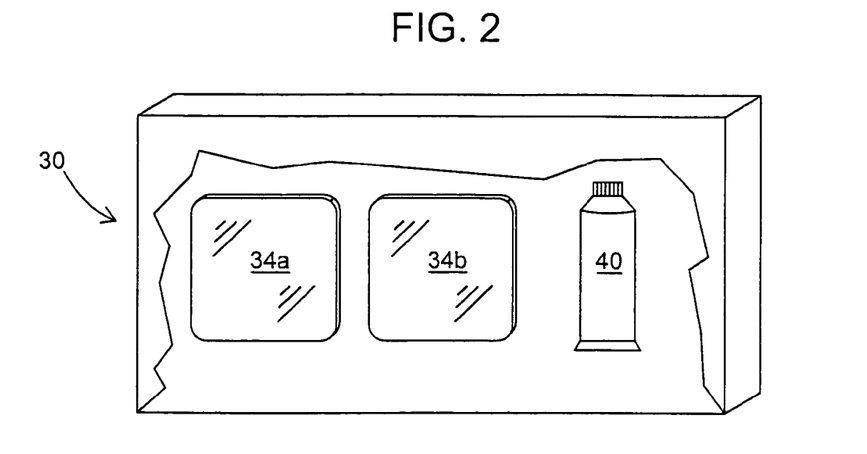
FIG. 2 shows an exemplary embodiment of a subject kit having two hydrogel patch debridement compositions and a single dosage amount of an active agent.

The dosage amount of a given active agent provided in a kit may be sufficient for a single application or for multiple applications. Accordingly, in certain embodiments of the subject kits a single dosage amount of one or more active agents is present in a kit. For example, a kit may include two or more hydrogel patch debridement compositions and a single dosage amount of an active agent. FIG. 2 shows an exemplary embodiment of a subject kit 30 (front view-cut away) that includes two hydrogel patch debridement compositions 34a and 34b and a single dosage amount of an active agent 40.

Figure 3:
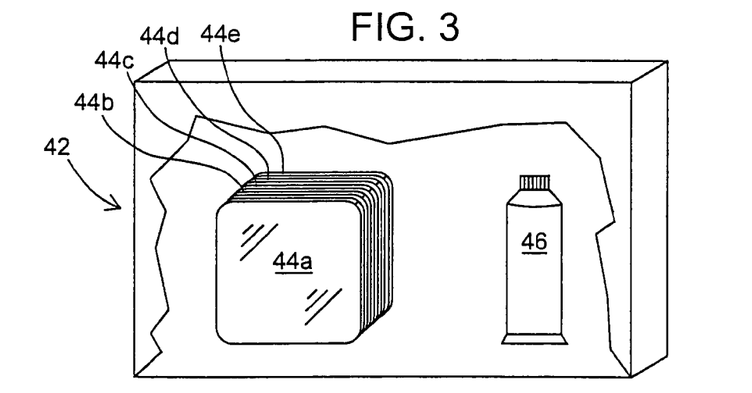
FIG. 3 shows an exemplary embodiment of a subject kit having a plurality of hydrogel patch debridement compositions and a single container having multiple dosage amounts of an active agent.
Figure 4:
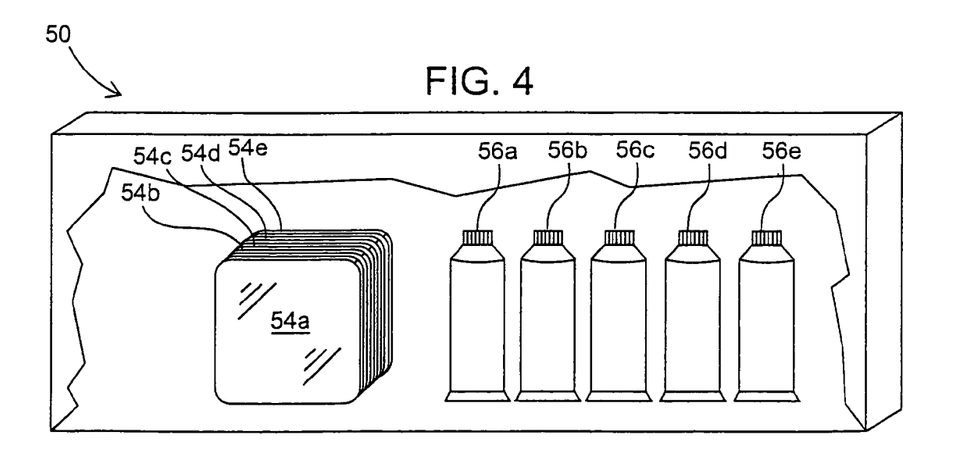
FIG. 4 shows an exemplary embodiment of a subject kit having a plurality of hydrogel patch debridement compositions and a plurality of containers of an active agent.

In certain other embodiments, multiple dosage amounts of an active agent may be present in a kit. For example, a kit may include two or more hydrogel patch debridement compositions and multiple dosage amounts of one or more active agent. In those embodiments having multiple dosage amounts of an active agent, such may be packaged in a single container, e.g., a single tube, bottle, vial, and the like, or one or more dosage amounts may be individually packaged such that certain kits may have more than one container of an active agent. FIG. 3 shows an exemplary embodiment of a subject kit 42 (front view—cut away) that includes a plurality of hydrogel patch debridement compositions 44a-44e and multiple doses of an active agent 46. While kit 42 is shown having five hydrogel patch debridement compositions, it shall be understood that fewer (i.e., at least two) or more hydrogel patch debridement compositions may be included in a kit and additional active agents may be included (in single or multiple dosages). As mentioned above, in certain embodiments; more than one container of an active agent is provided in a kit. FIG. 4 shows an exemplary embodiment of a subject kit 50 (front view—cut away) that includes a plurality of hydrogel patch debridement compositions 54a-54e and multiple containers 56a-56e of active agent, where each container may include a single or multiple dosage amounts of an active agent and some or all of the active agents may be the same or some or all may be different. While kit 50 is shown having five hydrogel patch debridement compositions and five containers of active agent, it shall be understood that fewer (i.e., at least two) or more hydrogel patch debridement compositions and/ or fewer or more containers of active agent may be included in a kit.

In certain embodiments of the subject kits, the hydrogel patch debridement compositions and optional active agent(s) are packaged in a kit containment element to make a single, easily handled unit, where the kit containment element, e.g., box or analogous structure, may or may not be an airtight container, e.g., to further preserve the composition of the patches and active agent, if present, until use.

The following examples are offered by way of illustration and not by way of limitation.

Experimental

I. Summary of Japanese Industrial Standards Test Z-0237 (i.e., JIS Z-0237) used to Quantify Adhesiveness of a Hydrogel Patch Composition

| Steel balls for adhesive strength measurement | | |
|---|---|---|
| No. | Diameter (mm) | Weight (g) |
| 1 | 3.2 | 0.13 |
| 2 | 4.8 | 0.45 |
| 3 | 6.3 | 1.0 |
| 4 | 7.9 | 2.0 |
| 5 | 9.5 | 3.5 |
| 6 | 11.1 | 5.6 |
| 7 | 12.7 | 8.3 |
| 8 | 14.3 | 11.9 |
| 9 | 15.9 | 16.3 |
| 10 | 17.5 | 21.7 |
| 11 | 19.1 | 27.2 |
| 12 | 20.6 | 35.8 |
| 13 | 22.2 | 44.8 |
| 14 | 23.8 | 55.0 |

B. The Adhesive Strength Test Procedure

A sheet of the preparation to be tested is first placed, adhesive side up, on a level support of 30 cm long at an angle 30 degree to the horizon with the adhesive side up. Next, the top 10 cm and the bottom 15 cm of the exposed adhesive side of the preparation are covered with paper, leaving the central 5 cm portion adhesive exposed. Next, a steel ball is allowed to roll down the structure from the top end. If a given ball stops for 5 seconds or longer on the adhesive side, the adhesiveness of the preparation is determined as being adhesive at least for balls of that dimension or less.

II. Debridement Assay

A. Hydrogel Patch Composition

A hydrogel patch composition having the following hydrogel composition was prepared.

| Ingredient | Concentration(%)(w/w) |
|---|---|
| Methyl Paraben | 0.15 |
| Propylene Glycol | 5 |
| Gelatine | 1.05 |
| Polyvinyl Alcohol | 0.42 |
| 70% Sorbitol Solution | 20 |
| Kaoline | 1.5 |
| Polyacrylic Acid | 2 |
| Glycerin | 18 |
| Cellulose Gum | 5 |
| Dihydroxyaluminum amino acetate | 0.07 |
| Sodium Polyacrylate | 5 |
| Tartaric Acid | 0.5 |
| Urea | 3 |
| EDTA | 0.05 |
| Water | 38.26 |
| Total | 100.00 |

The composition had a pH of 6.0. The composition placed on a PET film liner and PET non-woven fabric backing. The base weight was 100 g/square meter.

The composition had an adhesive strength, as determined using the JIS Z-0237 assay described in Example I, above, of No.9 Steel ball (16.3 g) (stopped).

B. Debridement Assay

1. Materials and Methods

Animal Model: Sprague Dawley Rat

Hydrogel Debridement Patch Composition (as described in II.A. above)

Size: 10 cm×14 cm, Base weight: 1000 g/square meter

Adhesive strength: No.9 Steel ball (16.3 g) stopped

Unwanted matter: Sand having a fine grain particle size is less than 0.5 mm diameter)

2. Procedure

The hair of on the back of the rat is shaved close to the skin. Next, several scratch wounds are made on the shaved back of the rat with a hypodermic needle. A quantity of sand is then placed on the scratch and around it.

In the following debridement procedure, two hydrogel debridement compositions were employed. In the procedure, a first hydrogel debridement composition is contacted with the skin wound and removed. The amount of sand removal is then determined. The same procedure is then employed for a second hydrogen debridement composition.

The amount of sand removed from the wound is determined visually according to the following scale:

Grades

6+: 99% or more sand removal from scratch wounds and around wound (Skin and wound are clean).

5+: 90% or more sand removal from scratch wounds and around wound (Skin and wound are mostly clean).

4+: 80% to less than 90% sand removal from scratch wounds and around wound.

3+: 70% to less than 80% sand removal from scratch wounds and around wound.

2+: 50% to less than 70% sand removal from scratch wounds and around wound.

1+: less than 50% sand removal from scratch wounds and around wound.

| Results | |
|---|---|
| No1 | |
| The first debridement treatment | 5+ |
| Second debridement treatment | 6+ |
| No2 | |
| The first debridement treatment | 4+ |
| Second debridement treatment | 6+ |
| No.3 | |
| The first debridement treatment | 5+ |
| Second debridement treatment | 6+ |

The above results demonstrate that hydrogel debridement removed the unwanted material without damage to the skin and wound. While the adhesiveness of the hydrogel debridement composition had a strength of No.9 steel ball, in certain embodiments, the results are obtained with adhesive strengths less than No. 9, e.g., No. 8, No. 7, No. 6., No 5., No. 4, No. 3, No. 2 or even No. 1. However, in representative embodiments, the adhesive strength is at least about No. 3, e.g., at least about No. 4. The above results demonstrate that hydrogel debridement works and is a tissue friendly manner.

It is evident from the above results and discussion that the subject invention provides for the effective debridement of wounds without mechanical or chemical insult to the wound. Furthermore, the subject invention has a broad range of diverse applications, where such applications include the debridement of a variety of different types of wounds including deep and superficial wounds, open- and closed-skin wounds, large and small wounds, wounds produced by a variety of different causes, etc. Furthermore, the subject methods are easily tolerable by a subject, i.e., do not produce undue pain to a subject. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of debriding a skin wound, the method comprising:
   contacting said skin wound with an adhesive hydrogel patch debridement composition; and
   removing said adhesive hydrogel patch debridement composition from said skin wound to remove foreign matter from said skin wound to debride said skin wound.

2. The method of claim 1, wherein said hydrogel patch debridement composition is contacted with said wound for a period of time of about 10 seconds or more.

3. The method of claim 2, wherein said hydrogel patch debridement composition is contacted with said wound for a period of time that ranges from about 30 seconds to about 5 hours.

4. The method according to claim 1, wherein said method comprises sequentially contacting said wound with at least a first and second hydrogel patch debridement composition.

5. The method of claim 1, further comprising applying an active agent to said skin wound.

6. The method of claim 5, wherein said active agent is integrated in said hydrogel patch debridement composition.

7. The method of claim 5, wherein said active agent is separate from said hydrogel patch debridement composition.

8. The method of claim 5, wherein said active agent is at least one of antimicrobial, anti-infective, antiseptic, antiinflammatory, nonsteroidal antiinflammatory agent, anesthetic, analgesic, antifungal, antimycotic, antiparasitic, antiviral, enzyme, enzyme inhibitor, growth factor, steroid, insulin, aloe vera, herbal extract, collagen, vitamin, mineral, hyaluronic acid salts and derivatives, glucocorticoid, antihistaminic, antioxidant, calmodulin, protein kinase C, calcium channel blocker and desoxyribonucleoside.

9. The method of claim 1, wherein said hydrogel patch debridement composition comprises:
   (a) a water-soluble polymer gel;
   (b) water; and
   (c) a water retaining agent.

10. The method of claim 1, wherein said skin wound is at least one of ulcer, burn, bone infection, gangrene, laceration, abrasion, incision, avul, amputation, post-operative infection, surgical wounds, brown recluse spider wound, failing or compromised skin/muscle grafts or flap, bite, slash wound and bruise.

11. The method of claim 1, wherein said hydrogel patch debridement composition is contacted with at least one of: arm, hand, trunk, leg, foot, ankle, face, neck, scalp and torso.

12. The method according to claim 1, wherein said method removes at least about 50% unwanted subject matter from said wound.

13. The method according to claim 12, wherein said method removes at least about 70% unwanted subject matter from said wound.

14. The method according to claim 13, wherein said method removes at least about 90% unwanted subject matter from said wound.

15. The method according to claim 1, wherein said foreign matter is selected from dirt, tar, gravel, grease, oil, maggots, paper, and metal.

16. The method according to claim 1, wherein said adhesive hydrogel patch debridement composition comprises water ranging from about 25% (w/w) to about 90%.

17. The method according to claim 1, wherein said adhesive hydrogel patch debridement composition is sufficiently adhesive to stop at least a No. 3 size ball as determined using the Japanese Industrial Standards (JIS) Z-0237 adhesive strength measurement protocol.

18. The method according to claim 1, wherein said hydrogel patch debridement composition is contacted with said wound for 2 hours or less.

* * * * *